(12) United States Patent
Tu et al.

(10) Patent No.: US 6,228,109 B1
(45) Date of Patent: *May 8, 2001

(54) METHODS FOR TREATING ATHEROSCLEROSIS AND VULNERABLE PLAQUES

(76) Inventors: Lily Chen Tu; Hosheng Tu, both of 2151 Palermo, Tustin, CA (US) 92782

(*) Notice: Subject to any disclaimer, the term of this patent is extended or adjusted under 35 U.S.C. 154(b) by 0 days.

This patent is subject to a terminal disclaimer.

(21) Appl. No.: 09/390,951

(22) Filed: Sep. 7, 1999

Related U.S. Application Data

(63) Continuation-in-part of application No. 09/143,890, filed on Aug. 31, 1998, now Pat. No. 5,980,563.

(51) Int. Cl.[7] .................................................. A61F 7/12
(52) U.S. Cl. ........................... 607/113; 607/99; 607/101; 606/41

(58) Field of Search ..................... 606/41, 42; 607/96, 607/98, 99, 101–102, 113

(56) References Cited

U.S. PATENT DOCUMENTS

| | | | |
|---|---|---|---|
| 5,078,736 | * | 1/1992 | Behl ........................................ 623/1 |
| 5,178,618 | * | 1/1993 | Kandarpa ............................... 606/28 |
| 5,775,338 | * | 7/1998 | Hastings ................................ 128/898 |

* cited by examiner

Primary Examiner—Linda C. M. Dvorak
Assistant Examiner—Roy Gibson (57) ABSTRACT

A method using an ablation apparatus for treating tissues or atherosclerosis on a patient having a pre-implanted medical stent, the method including applying RF energy to the tissue lesion site underlying the stent for therapeutic purposes at different energy levels, different post-procedure times, and different modes of energy delivery.

5 Claims, 5 Drawing Sheets

METHODS FOR TREATING ATHEROSCLEROSIS AND VULNERABLE PLAQUES

CROSS-REFERENCE TO RELATED APPLICATION

This application is a continuation-in-part of application Ser. No. 09/143,890, filed Aug. 31, 1998, now U.S. Pat. No. 5,980,563; the entire contents of which are incorporated herein by reference.

TECHNICAL FIELD OF THE INVENTION

The present invention generally relates to improved medical apparatus and methods for treating vascular tissues, and more particularly, to such an ablation apparatus and methods for treating atherosclerosis or tissues in a patient by delivering therapeutic RF energy at least one time through a metal stenting element to the specific lesion sites.

BACKGROUND OF THE INVENTION

An artery is one of the tube-shaped blood vessels that carry blood away from the heart to the body's tissues and organs. An artery is made up of outer fibrous layer, smooth muscle layer, connecting tissue and the inner lining cells. If arterial walls become hardened due to the accumulation of fatty substances, then blood flow can diminish. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through the artery until it reaches the blocked area. The balloon is then inflated, flattening the plaque and increasing the diameter of the blood vessel opening. The arterial passage is thus widened. As a result of enlarging the hardened plaque, cracks may unfortunately occur within the plaque to expose the underlying fresh tissue or cells to the blood stream.

There are limitations, however, to this technique's application, depending on the extent of the disease, the blood flow through the artery, and the part of the anatomy and the particular vessels involved. Plaque build-up and/or severe re-stenosis recurs within 6 months is up to 30–40 percent of those treated. Balloon angioplasty can only be characterized as a moderate-success procedure. Recently, a newer technique of inserting a metallic stenting element is used to permanently maintain the walls of the vessel treated at its extended opening state. Vascular stents are tiny mesh tubes made of stainless steel or other metals and are used by heart surgeons to prop open the weak inner walls of diseased arteries. They are often used in conjunction with balloon angioplasty to prevent restenosis after the clogged arteries are treated. Stenting procedure reduces the probability of restenosis; however, the success rate is still sub-optimal. The underlying ruptured fresh tissue or denuded cells still pose as a precursor for vessel reclosures or angio-spasm. Neointima and/or intimal hyperplasia through the openings of the expanded stent meshes as a result of plaque rupture and/or tissue injury remains a major cause for stent restenosis.

When a clogged artery is widened, the plaque is broken up and the underlying collagen or damaged endothelium is exposed to the blood flow. Collagen has a prothrombotic property that is part of body healing process. Unless the collagen or the damaged endothelium is passivated or modulated, the chance for blood vessel clotting as well as restenosis exists. Moderate heat is known to tighten and shrink the collagen tissue as illustrated in U.S. Pat. Nos. 5,456,662 and 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998).

Therefore, it becomes imperative to post-treat vessel walls after the walls are treated with angioplasty and/or stenting procedures. Since the freshly exposed collagen or denuded endothelium is partially passivated or modulated via the post-treatment method, a thermal energy post-treatment therapy comprising multiple treatment periods following angioplasty and/or stenting to completely mitigate the intimal hyperplasia for the subsequent elimination of restenosis becomes clinically necessary. For example, a first thermal energy post-treatment may be done immediately after the stenting procedure to take advantage of the operational setup for the patient. A second thermal energy post-treatment may also be done to the same patient at about one to two weeks post-operationally when the patient recovers from the stenting operation.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment apparatus have an advantage because of the use of a therapeutic energy that is rapidly dissipated and reduced to a non-destructive level by conduction and convection or other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism or software algorithm, can be supplied precisely to the apparatus-to-tissues contact site to obtain the desired temperature for treating a tissue.

A stent deployed within a vessel, such as a coronary stent, has excellent metal-to-tissue contact surface. It becomes an ideal medium for applying thermal energy to the tissue needed for treatment or modulation. In the case of angioplasty alone, the enlarged blood vessel still needs certain metallic contact surface for delivering the RF thermal energy to the denuded collagen or damaged endothelium. A temporary or an expandable/retractable metallic stenting element is useful in this case to shrink and tighten the target tissue. Therefore, there is a need for an improved medical apparatus having the capability to effectively contact the desired inner walls of a tubular vessel using the radiofrequency energy to treat an enlarged artery, veins or other tissues, such as esophagus, larynx, ureter, urethra and the like.

SUMMARY OF THE INVENTION

In general, it is an object of the present invention to provide a method and an improved medical ablation apparatus for generating heat, to treat the atherosclerosis, vascular vessels, or other tissues, such as intestine, colon, ureter, uterine tube, and the like. It is another preferred object of the present invention to provide a method for repeatedly generating heat to treat the atherosclerosis at different post-procedure times. It is another object of the present invention to provide a method and an apparatus for monitoring the temperature of the ablated tissue, and to control the temperature by utilizing a temperature control mechanism and/or algorithm. The location of the temperature sensor means is preferably at close proximity of the electrode means of the ablation apparatus. It is still another object of this invention to provide a method and an apparatus for treating atherosclerosis, vascular walls, or tubular cellular tissues in a patient by applying RF current to a pre-implanted stent and consequently to the underlying tissues. It is still another preferred object of the present invention to provide a method by applying RF current to a pre-implanted stent and consequently to the underlying tissues at different post-procedure times.

Briefly, heat is generated by supplying a suitable energy source to an apparatus, which is comprised of at least one electrode means for providing energy, in contact with the body tissues through a pre-implanted stent. A "pre-implanted stent" is defined in this invention as any metallic stenting element, in mesh form, coil form or other appropriate form, used to enlarge and maintain the enlarged tissues or vessels. Examples include coronary stent, peripheral stent, uterine stent and the like. A suitable energy source may consist of radiofrequency energy, microwave energy, ultrasonic energy, alternating current energy, or laser energy. The energy can be applied to the stent and consequently to the atherosclerosis, vascular walls, or cellular tissues through the electrode means. A DIP (dispersive indifferent pad) type pad or electrode, that contacts the patient, is connected to the Indifferent Electrode Connector on the RF generator. Therefore, the RF energy delivery becomes effective when a close circuit from a RF generator through a patient and returning to the RF generator is formed. When using an alternating current outlet, the generator should be grounded to avoid electrical interference. Heat is controlled by the power of the RF energy delivered and by the delivery duration. The standard RF energy generator means and its applications through the electrode means, to a patient are well known for those who are skilled in the art.

In an optional embodiment, means for generating vibration at the distal section comprises a motor mounted in the cavity of the handle, which has a rotatable motor shaft, an elongated connecting shaft having a first end, to which the distal end portion is connected, and a second end connected to the handle, a weight eccentrically mounted on the motor shaft with respect to the motor shaft axis, so as to rotate eccentrically, so that when the motor shaft rotates, the distal end portion of the apparatus vibrates. The mechanical vibration by using a rotating motor is distinctly different from the ultrasonic vibration because ultrasonic vibration is at a much higher frequency and lower amplitude.

In one embodiment, the apparatus comprises a deployable wire electrode or plurality of wire electrodes. In a preferred embodiment, the wire electrode is a spiral wire electrode having the next spiral always larger than the prior spiral, so that resilience and semi-compressibility becomes the property of the wire electrode to ultimately deploy to its full extent. The deployed wire electrode is to intimately contact a pre-implanted stent at any contact point and subsequently the stent becomes an electrode means because the stent contacts the tissues behind itself. The wire electrode of the present invention is connected through an electrical conductor to an external RF generating means for generating RF energy. In the case of a wire electrode inside a tubular vessel, the wire electrode is preshaped and extends to its maximum distance radially to contact the pre-implanted stent. The wire electrode is semi-compressible so that when the deployed wire is pressed against the stent, an appropriate pressure is exerted onto the stent to ensure intimate contact when applying the RF energy therapy. Because of the continuous process of intimal hyperplasia and neointima growth at the tissue injury sites, the thermal energy therapy may be applied at different energy levels, different post-procedure times, and different modes of energy delivery.

The method and medical apparatus of the present invention has several significant advantages over other known systems or techniques to treat the atherosclerosis or tissues having a pre-implanted stent or an electrode means for delivering RF energy to the atherosclerosis. In particular, the apparatus system comprising the extendible wire electrode means, using RF energy as a heat source, in this invention and simultaneously applying pressure to the pre-implant stent, results in a more efficient therapeutic effect, which is highly desirable in its intended application on the atherosclerosis or on other tissue ablation applications when there is a pre-implanted stent.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 5, what is shown is an embodiment of the ablation apparatus system, comprising simultaneously applying radiofrequency energy and applying a pressure therapy to treat the atherosclerosis, vascular vessels, and/or other tubular cellular tissues of a patient through a pre-implanted stent.

Figure 1:
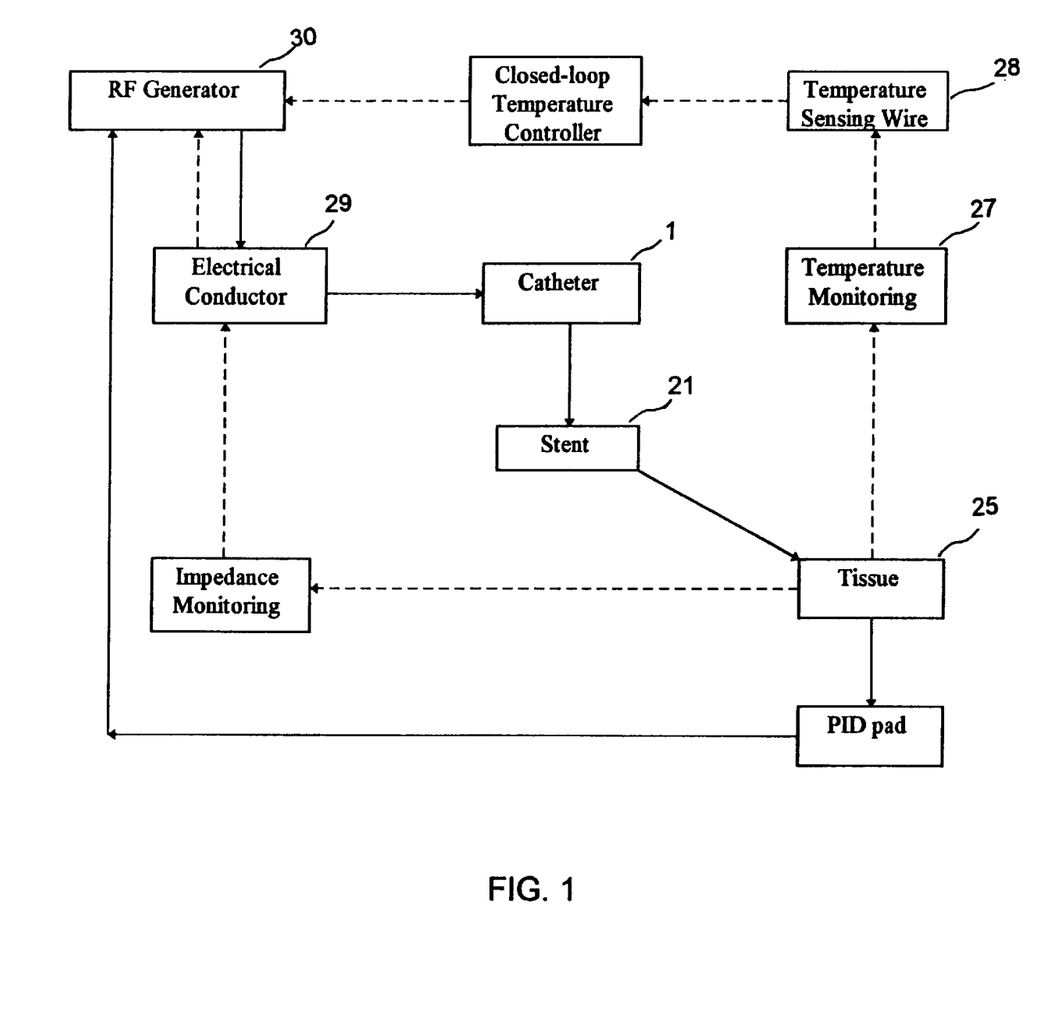
FIG. 1 is a schematic diagram of a RF treatment method in relation to the tissues or atherosclerosis through a pre-implanted metallic stent in a patient.

FIG. 1 shows a schematic diagram of a RF treatment method in relation to the tissues or atherosclerosis through a pre-implanted metallic stent in a patient. A RF generator 30 is connected to a catheter or an ablation apparatus 1 through an electrical conductor 29. A wire electrode 12 of the catheter or an ablation apparatus 1 is to contact a pre-implanted stent 21 when the apparatus is deployed. The stent is in close contact with the underlying tissue 25. A DIP (dispersive indifferent pad) type pad, that contacts the patient, is connected to the Indifferent Electrode Connector mounted on the RF generator 30. Therefore, the RF energy delivery becomes effective when a close circuit from a RF generator through a patient and returning to the RF generator is formed. In one embodiment, impedance measured from the tissue contact is to ensure good tissue contact for ablation, otherwise the RF power is cut off when the impedance is unreasonably high. A temperature sensor 27 is also used to measure the tissue temperature and is relayed through a temperature sensing wire 28 and a closed-loop temperature controller for controlling the ablative energy delivered. Heat is controlled by the power of the RF energy delivered and by the delivery duration. Energy delivery can also be controlled by a software algorithm without sensed temperature inputs.

Figure 2:
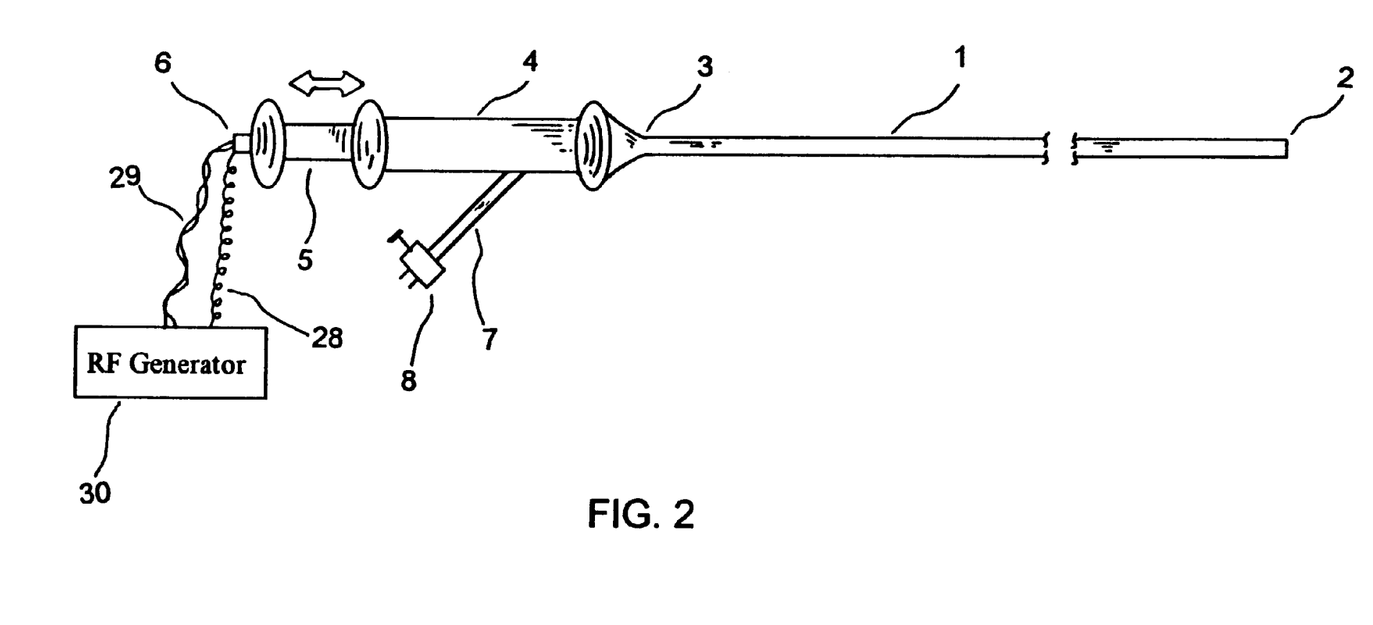
FIG. 2 is an overall view of the ablation apparatus having a deployable wire electrode and a RF generator, constructed in accordance to the principles of the present invention.

As shown in FIG. 2, the ablation apparatus system in the form of an elongate tubular assembly 1 comprises a flexible tubular shaft having a distal section, a distal end 2, a proximal end 3, and at least one lumen 10 or 11 extending therebetween, wherein the at least one lumen has at least one opening at the distal end of the tubular shaft 1. A handle 4 is attached to the proximal end 3 of the tubular shaft, wherein the handle 4 has a cavity. A hollow tubing 7 having a passageway and a locking valve 8 is attached to the handle 4, wherein the passageway is connected to the at least one lumen 11 of the tubular shaft 1. An elongate tubular element is located inside the at least one lumen 10 of the tubular shaft 1, wherein the elongate tubular element comprises a distal end 13 and a proximal end, and wherein the distal end 13 comprises a preshaped spiral wire electrode 12.

In one embodiment, the spiral wire electrode has a plurality of spirals, whereby the diameter of the next spiral is larger than that of the prior spiral. An electrode deployment mechanism 5 is mounted on the handle 4, wherein the electrode deployment mechanism is attached to the proximal end of the elongate tubular element. A RF energy generating means 30 is part of the ablation apparatus system, wherein the RE energy is provided to the spiral wire electrode 12 for therapeutic purposes through the conducting wire 29 and the connector 6 at the proximal end of the handle 4.

Figure 3:
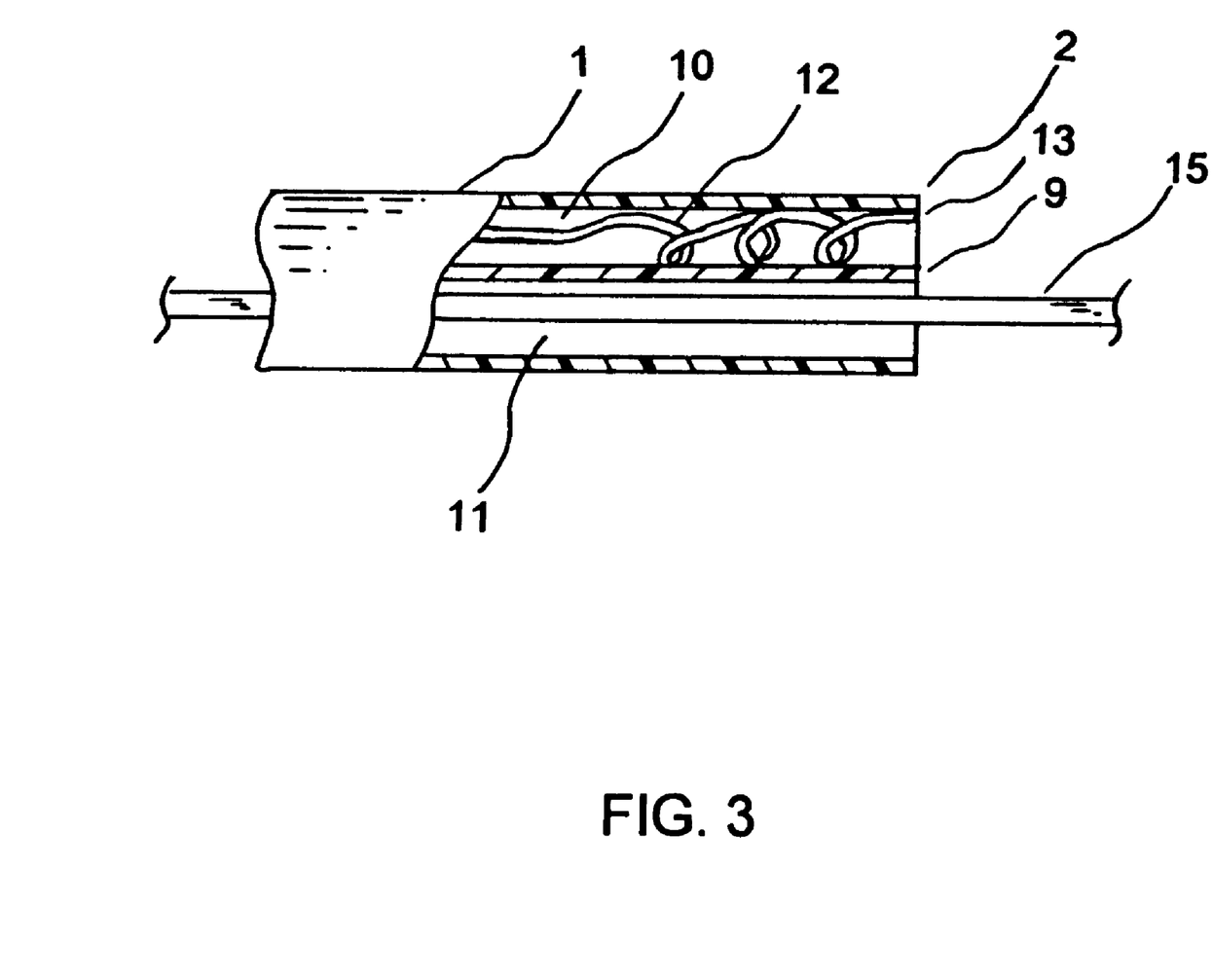
FIG. 3 is a cross-sectional view of the distal end portion of the apparatus, having a deployable wire electrode positioned within the lumen of the elongated tubular shaft, at a non-deployed state.

FIG. 3 shows a cross-sectional view of the distal end portion of the apparatus 1, including a deployable wire electrode 12. Under a non-deployed state, the deployable wire electrode 12 is retracted inside the lumen 10 of the distal end portion. The wire end 13 is located just within the distal end 2 of the tubular shaft 1. In one embodiment, the distal end has two lumens 10 and 11. One lumen 10 is used by the deployable wire electrode 12 for creating an ablation means in association with the pre-implanted stent 21. The other lumen 11 is used to tract a previously inserted guidewire 15 to the lesion site. The apparatus 1 of the present invention rides on the existing guidewire 15 to the target site 24 for ablation operation.

An insulated electrical conductor 29 or the elongate tubular element itself as a conducting means passes through the lumen 10 of the shaft 1 and is connected to the wire electrode means 12. The other end of the electrical conductor means is connected to an external RF generator 30.

Figure 4:
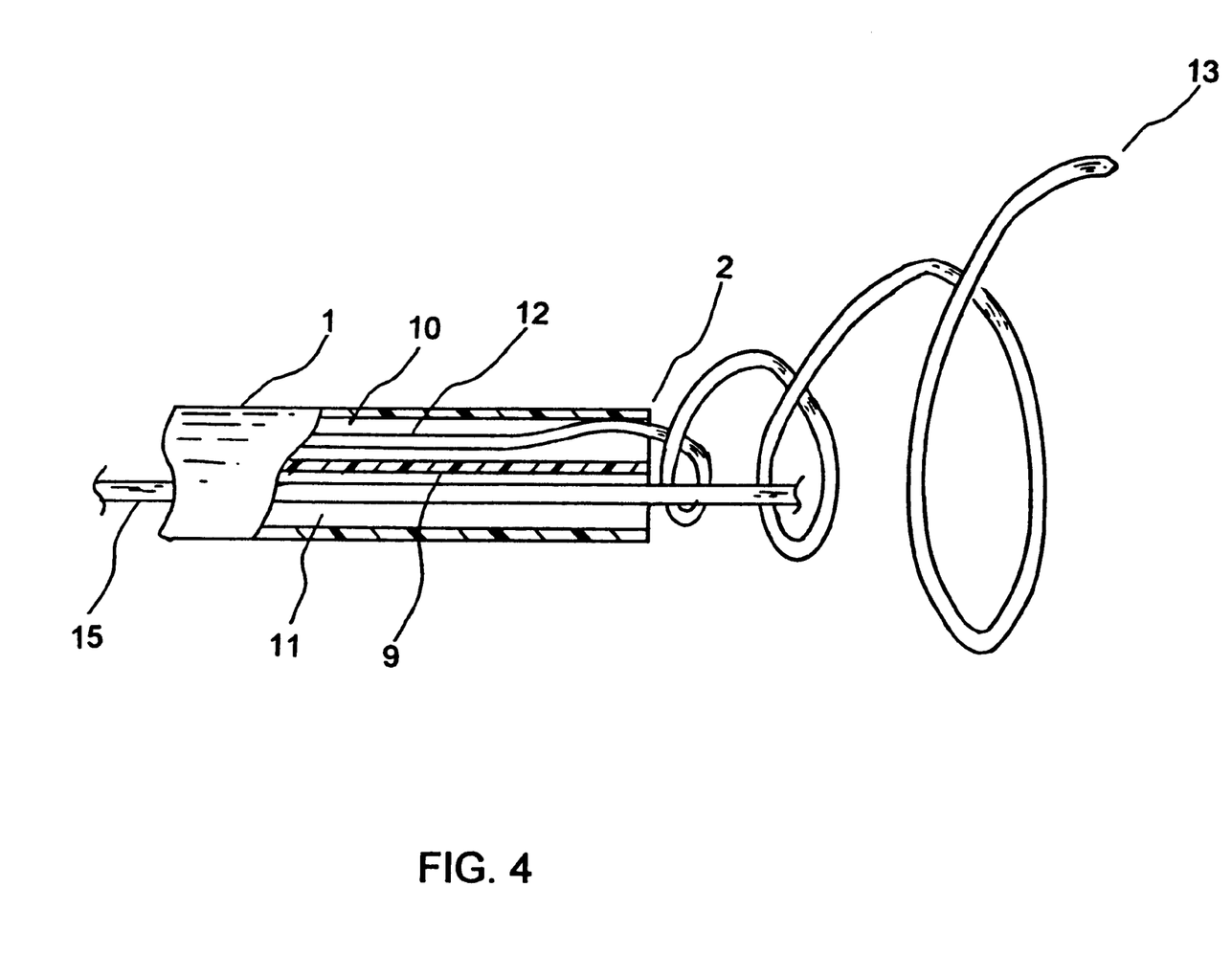
FIG. 4 is a cross-sectional view of the distal end portion of the apparatus, having a deployable wire electrode being deployed to its full extent, at a deployed state.

FIG. 4 shows a cross-sectional view of the distal end portion of the tubular shaft 1 at a deployed state. The deployment operation is initiated at the electrode deployment mechanism 5 at the handle 4. The deployed wire electrode 12 is fully extended radially to contact the radially inner surface of a pre-implanted stent 21. This distal portion of the deployed wire electrode and its surface is made of conductive material, which is connected to the RF energy source through an insulated electrical conductor. Other portion of the tubular shaft and surface of the apparatus is not conductive. In one embodiment, the radially fully extendible spiral wire electrode 12 is preferably extended radially at least twice the diameter of the tubular shaft 1.

In one embodiment, at least one temperature sensing means 27 for sensing the surrounding temperature is disposed at close proximity of the wire electrode 12. Insulated temperature sensor wire means 28 for transmitting temperature data passes from the temperature sensing means 27, to an external temperature control mechanism through the outlet connector 6. The RF energy delivery is controlled by using the measured temperature from the temperature sensing means 27, through a closed-loop temperature control mechanism and/or a software algorithm. When the measured temperature rises to the preset high-limit point, the temperature control mechanism sends out a signal to cut off the RF energy supply. In a similar manner, when the measured temperature drops to the preset low-limit point, the temperature control mechanism sends out a signal to activate the RF energy supply.

Figure 5:
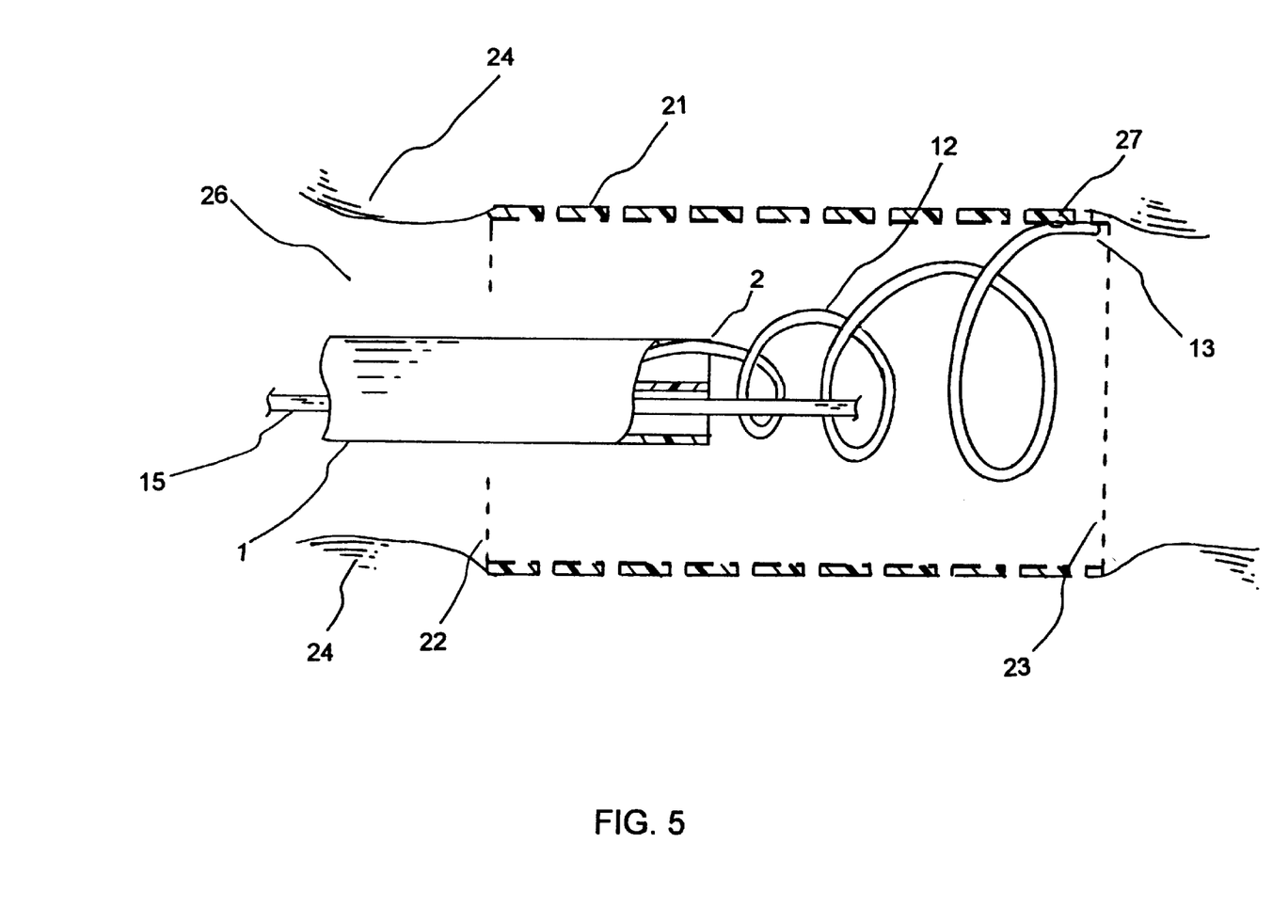
FIG. 5 a perspective view of the tissue underlined behind a pre-implanted stent being treated by the ablation apparatus of the present invention.

FIG. 5 shows a perspective view of a tissue 24 or atherosclerosis behind a pre-implanted stent 21 being treated by the medical ablation apparatus of the present invention. For illustrative purposes, the stenotic artery 26 having an arterial wall 24 is enlarged by an implanted stent 21 in a separate prior procedure. In one embodiment, the stent is bordered by two imaginary lines 22 and 23. To further passivate or modulate the collagen and/or the denuded endothelium cells, RF current is delivered to the wire electrode 12, whereby a portion of the wire electrode 12 contacts the stent 21 at a contact point 27 and forms a "stent-assisted" electrode to treat the atherosclerosis behind the stented region. In some particular embodiment, the electrode without a pre-implanted stent may also function as effectively to treat the atherosclerosis as the one with a "stent-assisted" electrode.

During procedures, the ablation apparatus is inserted into the body of a patient through natural opening or a surgical hole. A method for treating tissues of a patient having a pre-implanted medical stent, the method comprising the steps of (a) inserting an ablation apparatus through a natural opening to the location of the pre-implanted medical stent, wherein the ablation apparatus comprises energy means for delivering RF energy to the pre-implanted medical stent, the energy means comprising a RF energy generator, electrode means for contacting the pre-implanted medical stent, and at least one electrical conductor for transmitting RF energy from said RF energy generator to said electrode means; (b) positioning the electrode means by intimately contacting said electrode means with the pre-implanted medical stent; and (c) applying RE energy to the electrode means through the at least one electrical conductor to effect treatment of the tissues. The method may further comprise repeating the above RF therapy procedure for treating tissues at different energy level, different post-procedure times, different modes of therapy and the like.

The ablation apparatus may comprise a tubular shaft having a distal section, a distal end, a proximal end, and at least one lumen extending therebetween, wherein the at least one lumen has at least one opening at the distal end of the tubular shaft; a handle attached to the proximal end of the tubular shaft, wherein the handle has a cavity; a hollow tubing having a passageway and a locking valve attached to the handle, wherein the passageway is connected to the at least one lumen of the tubular shaft; an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of the next spiral is larger than that of the prior spiral; an electrode deployment mechanism mounted on the handle, wherein the electrode deployment mechanism is attached to the proximal end of the elongate tubular element.

As an alternative illustration, a method for treating atherosclerosis of a patient having a pre-implanted vascular stent, the method comprising the steps of (a) inserting an ablation apparatus through an artery or a vein to a location of the pre-implanted vascular stent, wherein the ablation apparatus comprises energy means for delivering RF energy to the pre-implanted vascular stent, the energy means comprising a RF energy generator, electrode means for contacting the pre-implanted vascular stent, and at least one electrical conductor for transmitting RF energy from said RF energy generator to said electrode means; (b) positioning the electrode means by intimately contacting said electrode means with the pre-implanted vascular stent; and (c) applying RF energy to the electrode means through the at least one electrical conductor to effect treatment of the atherosclerosis. The method may further comprise repeating the above RF therapy procedure for treating atherosclerosis at different energy level, different post-procedure times, different modes of therapy and the like.

In the above-referred embodiment, the ablation apparatus comprises a tubular shaft having a distal section, a distal end, a proximal end, and at least one lumen extending therebetween, wherein the at least one lumen has at least one opening at the distal end of the tubular shaft; a handle attached to the proximal end of the tubular shaft, wherein the handle has a cavity; a hollow tubing having a passageway and a locking valve attached to the handle, wherein the passageway is connected to the at least one lumen of the tubular shaft; an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of the next spiral is larger than that of the prior spiral; an electrode deployment mechanism mounted on the handle, wherein the electrode deployment mechanism is attached to the proximal end of the elongate tubular element.

The external RF energy generator means has the capability to supply RF energy by controlling the time, power, and temperature through an optional separate closed-loop temperature control means. The patient is connected to the RF generator means through a DIP electrode to form a closed-loop current system. Therefore, RF energy is applied and delivered to the targeted atherosclerosis region, through the electrode means of this invention, the "stent-assisted" electrode means The radiofrequency energy current in this invention is preferably within the range of 50 to 2,000 kHz. The delivered temperature at the tissue site is preferably slightly above the tissue denaturation temperature of about 65 to 80° C. The frequency of the vibration of the medical apparatus in this invention is preferably within the range of 60 to 1000 cycles per minute. By simultaneously applying RF energy to the electrode and by applying the pressure therapy, the atherosclerosis can be treated.

In a further embodiment, a method for treating atherosclerosis of a patient comprises the steps of (a) inserting an ablation apparatus through an artery or a vein to a location of a target tissue, wherein the ablation apparatus comprises energy means for delivering RF energy to the target tissue, the energy means comprising a RF energy generator, electrode means for contacting the target tissue, and at least one electrical conductor for transmitting RF energy from said RF energy generator to said electrode means; (b) positioning the electrode means by intimately contacting said electrode means on the target tissue; and (c) applying RF energy to the electrode means through the at least one electrical conductor to effect treatment of the target tissue.

In a particular embodiment, the material for the electrode means of this invention consists of conductive metals such as platinum, iridium, gold, silver, stainless steel, Nitinol, or an alloy of these metals.

In vivo, stent-assisted radiofrequency therapy can be performed relatively safely without significant electrical, hemodynamic or ischemic changes. The extent of heat-induced vessel wall passivation, elastic tissue straightening and periarterial myocardial necrosis are all related to the radiofrequency parameters and mode of therapy operations.

The ruptured collagen and/or denuded endothelium at the atherosclerotic plaque site may only be partially healed as a result of RF therapy of the present invention through the electrode to the pre-implanted stent to the underlying tissue. Therefore, a second time or third time of the RF therapy procedures is needed to thoroughly mitigate the neointima and/or intimal hyperplasia as a result of the earlier stenting procedure. It is generally well known that neointima is a continuous biological process once an injury prevails.

From the foregoing description, it should now be appreciated that a therapeutically ablation method for the tubular organs, atherosclerosis, and the treatment of vascular tissues, comprising a suitable energy source has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method for treating atherosclerosis of a patient having a pre-implanted vascular stent, the method comprising the steps of:
   (a) inserting an ablation apparatus through an artery or a vein to a location of the pre-implanted vascular stent, wherein the ablation apparatus comprises energy means for delivering RF energy to the pre-implanted vascular stent, the energy means comprising a RF energy generator, an electrode for contacting the pre-implanted vascular stent, and at least one electrical conductor for transmitting RF energy from said RF energy generator to said electrode;
   (b) positioning the electrode by intimately contacting said electrode with the pre-implanted vascular stent;
   (c) applying RF energy to the electrode through the at least one electrical conductor to effect treatment of the atherosclerosis; and
   (d) repeating steps (a) through (c) at a later time.

2. The method for treating atherosclerosis of a patient having a pre-implanted vascular stent as in claim 1, wherein the method step (d) comprises applying RF energy at a different energy level and/or at a different mode of RF energy application.

3. The method for treating atherosclerosis of a patient having a pre-implanted vascular stent as in claim 1, wherein the vascular stent is a coronary stent.

4. A method for treating tissues of a patient having a pre-implanted medical stent, the method comprising the steps of:

(a) inserting an ablation apparatus through a natural opening to the location of the pre-implanted medical stent, wherein the ablation apparatus comprises energy means for delivering RF energy to the pre-implanted medical stent, the energy means comprising a RF energy generator, an electrode for contacting the pre-implanted medical stent, and at least one electrical conductor for transmitting RF energy from said RF energy generator to said electrode;

(b) positioning the electrode by intimately contacting said electrode with the pre-implanted medical stent;

(c) applying RF energy to the electrode through the at least one electrical conductor to effect treatment of the tissues; and (d) repeating steps (a) through (c) at a later time.

5. The method for treating tissues of a patient having a pre-implanted medical stent as in claim 4, wherein the method step (d) comprises applying RF energy at a different energy level and/or at a different mode of RF energy application.

* * * * *